(12) United States Patent
Carr, Jr.

(10) Patent No.: US 11,413,404 B2
(45) Date of Patent: Aug. 16, 2022

(54) ELIMINATION OF VIRUSES IN BLOOD THROUGH MICROWAVE TECHNIQUES

(71) Applicant: Kenneth L. Carr, Jr., Woolwich, ME (US)

(72) Inventor: Kenneth L. Carr, Jr., Woolwich, ME (US)

( * ) Notice: Subject to any disclaimer, the term of this patent is extended or adjusted under 35 U.S.C. 154(b) by 0 days.

(21) Appl. No.: 17/406,556

(22) Filed: Aug. 19, 2021

(65) Prior Publication Data
US 2022/0054768 A1 Feb. 24, 2022

Related U.S. Application Data

(60) Provisional application No. 63/068,558, filed on Aug. 21, 2020.

(51) Int. Cl.
*A61M 5/44* (2006.01)
*A61M 1/36* (2006.01)
*H05B 6/80* (2006.01)

(52) U.S. Cl.
CPC .............. *A61M 5/44* (2013.01); *A61M 1/369* (2013.01); *H05B 6/802* (2013.01); *A61M 2205/366* (2013.01); *A61M 2205/3606* (2013.01); *A61M 2205/3686* (2013.01)

(58) Field of Classification Search
None
See application file for complete search history.

(56) References Cited

U.S. PATENT DOCUMENTS

| | | | | |
|---|---|---|---|---|
| 5,073,167 A | * | 12/1991 | Carr | G01N 1/44 604/114 |
| 6,229,957 B1 | * | 5/2001 | Baker | A61M 5/44 219/482 |
| 6,587,732 B1 | * | 7/2003 | Carr | A61M 1/369 128/898 |

* cited by examiner

*Primary Examiner* — Manuel A Mendez
(74) *Attorney, Agent, or Firm* — Anthony D. Pellegrini

(57) ABSTRACT

Heat treatment apparatus for inactivating viruses in blood includes a series of four tubing coils with connectors at the opposite ends of the series for connecting the tubing to a blood source and a blood destination, a microwave heating chamber arranged to receive the first coil of the series, a dwell chamber to receive the second coil of the series, a cooling chamber adapted to receive the third coil of the series, and a microwave reheating chamber to receive the fourth coil of the series, with the first, second, and fourth chambers employing microwave energy for heating the blood as it flows within the coils and providing a radiometer circuit for monitoring the temperatures of the blood in the first, second, and fourth coils to produce first, second, and fourth temperature signals in response thereto, which is responded to by a controller to control the energy producing means to impart a selected time/temperature profile to the blood flowing through the tubing and to deliver that blood at a selected delivery temperature.

27 Claims, 2 Drawing Sheets

ELIMINATION OF VIRUSES IN BLOOD THROUGH MICROWAVE TECHNIQUES

CROSS REFERENCE TO RELATED APPLICATIONS

This application claims the benefit of the provisional patent application, U.S. Ser. No. 63/068,558 ("ELIMINATION OF VIRUSES IN BLOOD THROUGH MICROWAVE TECHNIQUES"), filed Aug. 21, 2020, by Carr, Kenneth L., and currently pending, which is hereby incorporated by reference.

BACKGROUND OF THE INVENTION

A common technique for warming blood is to pass the blood through plastic coils immersed in a warm water bath. This method has numerous drawbacks, one in particular being the slowness of operation and the volume of blood required to be warmed at one time.

Microwave heating has been employed in connection with the heating of blood and intravenous fluids. For example, a standard microwave oven has been used to warm the entire blood bag. However, it is virtually impossible to achieve uniform heating of the blood or other liquid due to both the non-uniform distribution of microwave energy within the oven and the inability, using microwaves, to heat at sufficient depths in a lossy material such as blood which has a high dielectric constant. A further problem associated with heating the entire blood bag in a microwave oven is the inability to monitor the temperature of the liquid, particularly at depths.

In the in-line warming apparatus of U.S. Pat. No. 5,073,167 (Carr '167), a support element in the form of a bobbin supports a length of IV tubing wound thereon. The tubing-bobbin assembly is inserted into a microwave heating cavity. A non-invasive, non-perturbing microwave temperature monitor is provided within the cavity for monitoring the temperature of liquid flowing in the IV tube. Temperature sensors are also provided external to the cavity, on the tubing inlet side and the tubing outlet side with respect to the cavity. Controls are provided for generating control signals representative of the inlet, cavity and outlet temperatures to control the power level of microwave energy delivered to the heating cavity.

In U.S. Pat. No. 5,919,218 (Carr '218), a cartridge comprises a bobbin around which fluid-carrying tubing is wound, forming a coil. The cartridge is positioned in a waveguide structure comprising a microwave heating cavity by placing the cartridge through an opening in the waveguide cavity and into the heating region of that structure such that the coil and fluid flowing therethrough are subjected to the fields produced in the waveguide structure. The bobbin and the tubing are made of dielectric materials which are relatively transparent to the microwave radiation in the cavity and are, therefore, unaffected by the radiation. The fluid flowing through the tubing is relatively lossy and is therefore heated by the microwave energy. By monitoring the temperature of the fluid in the tubing and controlling the energy in response to that temperature, precise warming of the fluid is achieved.

The cartridge itself comprises tubing support means which include a bobbin or spool for positioning in the heating cavity at the heating region thereof. The support means may also include a base adapted to seat against the waveguide structure and close the opening into the heating cavity, with the bobbin projecting into the cavity. Preferably, the base has an electrically conductive surface which, when the cartridge is seated on the waveguide structure, is substantially flush with, and forms an extension of, the waveguide structure wall to prevent energy losses at the opening.

The other main component of the cartridge is a selected length of tubing which is arranged to be wound around the bobbin to form a relatively tight coil. Preferably, at least the bobbin portion of the support means and the tubing are made of materials which are substantially transparent to the radiation from the microwave transmitter to minimize energy loss and to optimize controlled warming of the fluid flowing through the tubing. The bobbin portion of the cartridge may be elongated and may define an elongated oval or racetrack-shape course for the turns of tubing so that when the cartridge is seated in the waveguide structure, the tubing coil has straight segments which extend almost the entire distance between the two broader walls of the waveguide structure, i.e., parallel to the lines of the electric field produced in the heating cavity when the warming apparatus is in operation.

Further, the cartridge bobbin may be dimensioned and positioned within the waveguide structure so that all of the straight segments of the tubing coil extend parallel to the end wall of the waveguide structure and are spaced from that end wall a distance substantially equal to a quarter wavelength or integral multiple thereof at the microwave transmitter frequency. For this, the width of the bobbin may be such that the straight tubing segments on opposite sides of the tubing coil are spaced apart a quarter wavelength or multiple thereof. This places the fluid being warmed at locations in the heating region such that there is maximum coupling of energy into the fluid.

However, even with thermal sensing of inlet and outlet portions of the tubing that are external to the waveguide structure, there is insufficient awareness of the fluid temperature within the structure, which can lead to underheating or overheating.

"High-Temperature Short-Time (HTST) Heat Inactivation of HIV and Other Viruses In Human Blood," by S. E. Charm, et al., published in Vox Sang, 1992; 62:12-20, hereby incorporated by reference herein, discloses an HTST system specifically designed to inactivate HIV and other viruses in human blood. The system described there is limited to heating only a discrete 10 ml bolus of fluid, which is ineffective for continuous viral elimination. Still, the data obtained by the authors of that article are useful in establishing the feasibility of using microwave heating to deactivate viruses in blood and indicate that a high-level of virus inactivation with modest to no changes in blood components can be achieved with microwave exposure times of a fraction of a second to several seconds at a temperature between 75° C. and 85° C. With that temperature range, various viruses including HIV were reduced to less than the lowest detectable amount.

However, prior HTST systems, including the one described in the above paper, are disadvantaged in that they are basically batch systems. Some take a relatively long time to reach the process temperature; some require a relatively long hold up time at the process temperature; and some take a relatively long time to cool the process fluid to a non-destructive temperature.

U.S. Pat. No. 6,587,732 (Carr '732) discloses a heat treatment apparatus for inactivating viruses in blood products or in cannulae if a patient's blood is being processed extra-corporally in a manner similar to dialysis. While the apparatus disclosed therein overcomes many of the disadvantages of the prior art, there remains the impracticality of maintaining the blood at a virus destroying temperature for a long enough period of time to achieve effective virus destruction.

It is therefore shown that there is a need for an improved blood warming apparatus that can effectively heat blood to virus destroying temperatures without also damaging the blood itself.

It is therefore an object of the present invention to provide for an improved blood warming apparatus that can effectively heat blood to virus destroying temperatures without also damaging the blood itself.

It is a further object of the present invention to provide for an improved blood warming apparatus that can effectively heat blood sourced from a patient to virus destroying temperatures and then return the blood to normal body temperature for reintroduction into the patient.

It is yet a further object of the present invention to provide a method of destroying viruses in blood by high-temperature short-time heating of the blood on a continuous in-line basis.

It is yet a further object of the present invention to provide a high-temperature short-time microwave heating method which permits the shaping of the heating time and temperature parameters to provide heat destruction of virus activity while maintaining the functional constituency of the otherwise heat-sensitive blood.

Other objects of the present invention will be readily apparent from the description that follows.

SUMMARY

It is known that the destruction of viruses is based on their tolerance to elevated temperature, and the duration of their exposure to that temperature. Research conducted at the New York Blood Center and verified at the Mass General Hospital Blood Services proved the potential effectiveness of a very short exposure time of blood to a high temperature on the destruction of blood-borne infections that include Hepatitis, Syphilis, Aids and Ebola. In the New York Study, temperatures of +77° C. over six milliseconds resulted in a high level of virus kill while maintaining the activity and protein structure of the blood essentially intact.

In order to capitalize on these findings, the present invention is designed to very rapidly heat blood to a virus killing temperature and then maintain it at that temperature for an appropriate duration to achieve virus destruction, and then to rapidly cool the blood so as to prevent damage to the blood components, using flow rates up to 500 ml/minute.

The present invention is an improvement over the '732 apparatus. It includes a series of four tubing coils with connectors at the opposite ends of the series for connecting the tubing to the blood product source and the blood product destination, or preferably to a source of blood from a patient and a cannula delivering treated blood back to a patient. Each coil has a small priming volume, e.g., 4-5 ml. The first coil is situated in a microwave heating chamber, the second coil is situated within a dwell chamber used to maintain the blood at an elevated temperature, the third coil reposes in a cooling chamber, and the fourth coil is positioned in a further microwave heating chamber that may be similar to the first such chamber and is used to bring the temperature of the blood back to its initial temperature. As discussed, the dwell chamber may also be a microwave heating chamber.

The elevation of the temperature of the blood is controlled by microwave radiometric sensing. In view of the wide temperature ranges involved, Silicone IV tubing must be used. The diameter of the tubing must be small with respect to the wavelength of the heating frequency to insure that the heating of the flowing blood will be uniform. The cross section of the tubing must remain uniform and fixed throughout the system to prevent turbulence and, in turn, to avoid the creation of air emboli. The length of the tubing or the number of turns in the tubing in each of the chambers of the system is determined by the flow rate and the desired temperature change.

In the first coil, the blood is exposed to uniform microwave energy present in the first chamber which heats the blood to a temperature sufficient to deactivate any viruses present therein. The energy applied to the blood to cause viral inactivation is determined by the power applied to achieve the target temperature and the duration or time that the target temperature must be maintained to achieve viral inactivation. The first chamber is used to obtain the target temperature and the dwell chamber is used to obtain the required duration. The heated blood then flows through the third coil in the cooling chamber where it is immediately cooled, thereby defining the end of the duration of anti-viral treatment of the blood.

Using non-invasive radiometric temperature sensors, the temperature profile along the blood heating/cooling pathway is obtained and used to control the heating and dwell chambers to maintain a uniform delivery temperature despite variations of fluid parameters such as flow rate and inlet temperature. In this way, the blood heating time and temperature parameters may be controlled carefully to allow complete destruction of virus activity in the blood while maintaining the viability of the blood.

As noted above, in many cases it is desirable to route the blood through a fourth coil positioned in another microwave heating chamber. This allows the blood to be cooled in the cooling chamber to a temperature below the desired delivery temperature (i.e., below normothermic temperature) and then be heated somewhat so that the target temperature is approached from below (i.e., close to normothermic temperature). This allows optimum control over the blood delivery temperature. As is known, normothermic temperature is approximately 37° C.

A radiometer circuit is provided with respect to certain or all chambers for non-invasively monitoring the temperatures of the blood in the first and second coils to produce first and second temperature signals in response thereto. A controller responds to these temperature signals by controlling the energy producing means to impart a selected time/temperature profile to the blood flowing through the tubing and to deliver the blood at a selected delivery temperature. A fourth coil and a second heating chamber is provided to heat the blood to the delivery temperature following the cooling thereof.

In the prior apparatus reflected in the above patents, the transducer in the heating cavity receives signals from all of the windings in the cartridge and accordingly senses the average temperature of the fluid in the multiple windings rather than the temperature of the fluid just as the fluid exits the heating cavity. Still further, the two external transducers, four separate external radiometers and the multiple cables connecting the various temperature transducers to the radiometers, increase the overall complexity and footprint of the prior apparatus.

The present invention provides an advancement over the prior art by the inclusion of the use of a "dwell" chamber intermediate the microwave heating chamber and the subsequent cooling chamber. A re-warming chamber may be arranged after the cooling chamber, as described above.

The dwell chamber may be provided with radiometric temperature sensing capabilities to ensure that a target temperature is maintained within the blood conveyed in the respective tubing; if the temperature is too high, the blood can be damaged, whereas if the temperature is too low, viral inactivation will not be achieved. The dwell chamber may also be provided with microwave heating capabilities such as provided in conjunction with the first heating chamber. The heating capabilities within the dwell chamber may thus be selectively actuated in response to the sensed temperature to maintain a minimum desired temperature. In an alternative embodiment, the dwell chamber is thermally insulated to maintain blood passing therethrough at a desired temperature or range of temperatures, with supplemental heat added to the dwell chamber as needed. In this embodiment, the supplemental heat may be added by flowing heated liquid or gas into and through the dwell chamber, or by providing radiant heating elements within the dwell chamber.

A further alternative embodiment may include the use of a single loop coil or a coil of minimized loops within at least the heating and re-warming chambers, within the heating, dwell and re-warming chambers, or within all four chambers, including the heating, dwell, cooling, and re-warming chambers. By "single loop" it is meant a linear inlet section, a 180-degree semi-circular return section, and a linear return section. Such an arrangement may provide several advantages. First, radiometric temperature measurements non-invasively and more accurately reflect the temperature of the blood flowing through the respective portion of the flow path, whereas the temperature detected within multi-loop coils reflected an average temperature for those multiple coils. Second, single loop coils enable smaller priming volumes. Third, single loop coils present less flow resistance. A single loop coil may be used in one or more chambers while a multi-loop coil is used in another one or more chambers.

It may be desirable, however, to implement a multi-loop path within the cooling chamber to provide greater tube surface area, thus facilitating a greater degree of thermal flux. Temperature sensors associated with the cooling chamber are desirable in establishing whether a desired temperature range is being met. In the case of over-cooling, microwave heating capabilities associated with the dwell chamber may be actuated such that the blood exiting the cooling chamber and entering the re-warming chamber is at a higher, desired temperature. Alternatively, or in addition thereto, the rate of flow of the blood may be increased to limit the degree of cooling. This increase in flow rate may also require a contemporaneous adjustment to the degree of heating in the initial heating chamber, the dwell chamber, and the re-warming chamber.

The inlet blood temperature into the initial heating chamber is normally 37° C. The heating chamber raises the blood temperature to a target temperature. This temperature may be dependent upon the specific blood-borne virus(es) to be eliminated, and may be on the order of 75° C. to 85° C., with a temperature of 77° C. being preferred. Subsequent to the heating chamber, the dwell chamber is intended to maintain the blood at the target temperature, or within a given range with respect to the target temperature, as described above. The length of the tubing and the number of turns are determined by the desired length of time the blood needs to be held at the predetermined target temperature or range of temperatures in order to achieve viral inactivation. The cooling chamber cools the blood to a temperature range such as 30° C. or below. The re-warming chamber brings the blood back to body temperature, about 37° C., prior to re-introduction to the patient. Alternatively, if the treated blood is not to be immediately reintroduced into the patient, the final rewarming of the blood can be eliminated.

Centralized control over microwave heating and flow rate control, in response to radiometric temperature sensing throughout the multi-chamber system, enables a closed-loop system.

It is to be understood that the foregoing and following description of the invention is intended to be illustrative and exemplary rather than restrictive of the invention as claimed. These and other aspects, advantages, and features of the invention will become apparent to those skilled in the art after review of the entire specification, accompanying figures, and claims.

DETAILED DESCRIPTION OF THE INVENTION

In accordance with the present invention, a continuously moving column of blood from a patient is rapidly heated in a microwave heating chamber 22 to a temperature high enough to provide heat destruction of virus activity in the blood. The blood is then flowed into a second chamber 22' where the temperature achieved in the first chamber 22 is maintained for a predetermined amount of time to destroy the virus located in the blood. The blood is then moved into an in-line cooling chamber 34 where it is cooled to a non-destructive temperature. Preferably, the blood is cooled in the cooling chamber 34 below the selected delivery temperature and then routed to another in-line microwave heating chamber 22" which heats the blood precisely to the desired delivery temperature (e.g., normal body temperature, or about 37° C.). In this way, the delivery temperature is approached from below for optimum accuracy.

The blood is flowed through the successive chambers through IV tubing 12 whose internal diameter is preferably quite small, e.g. 0.096 in., with respect to the wavelength of the microwave heating frequency used for heating the blood, thereby ensuring uniform heating of the blood which is in constant motion through the tubing. Preferably also, the tubing 12 is formed as a cartridge unit with a series of coils which may be positioned in the chambers present in the apparatus 20. Further in accordance with the present invention, means are provided for monitoring the temperature of the moving blood as it enters and leaves the various chambers utilizing non-invasive radiometry with detection occurring at microwave frequencies. This enables noninvasive measurements at depth to occur while the blood is in motion through the tubing 12. The measured differential temperatures are then used to determine the power level required for heating in the first and second heating chambers.

Using the in-line high temperature short time heating method described herein, a time/temperature profile may be produced in the moving column of blood to provide maximum heat destruction of virus activity while maintaining the functional constituency of the blood and product delivery at the proper delivery temperature.

Figure 1:
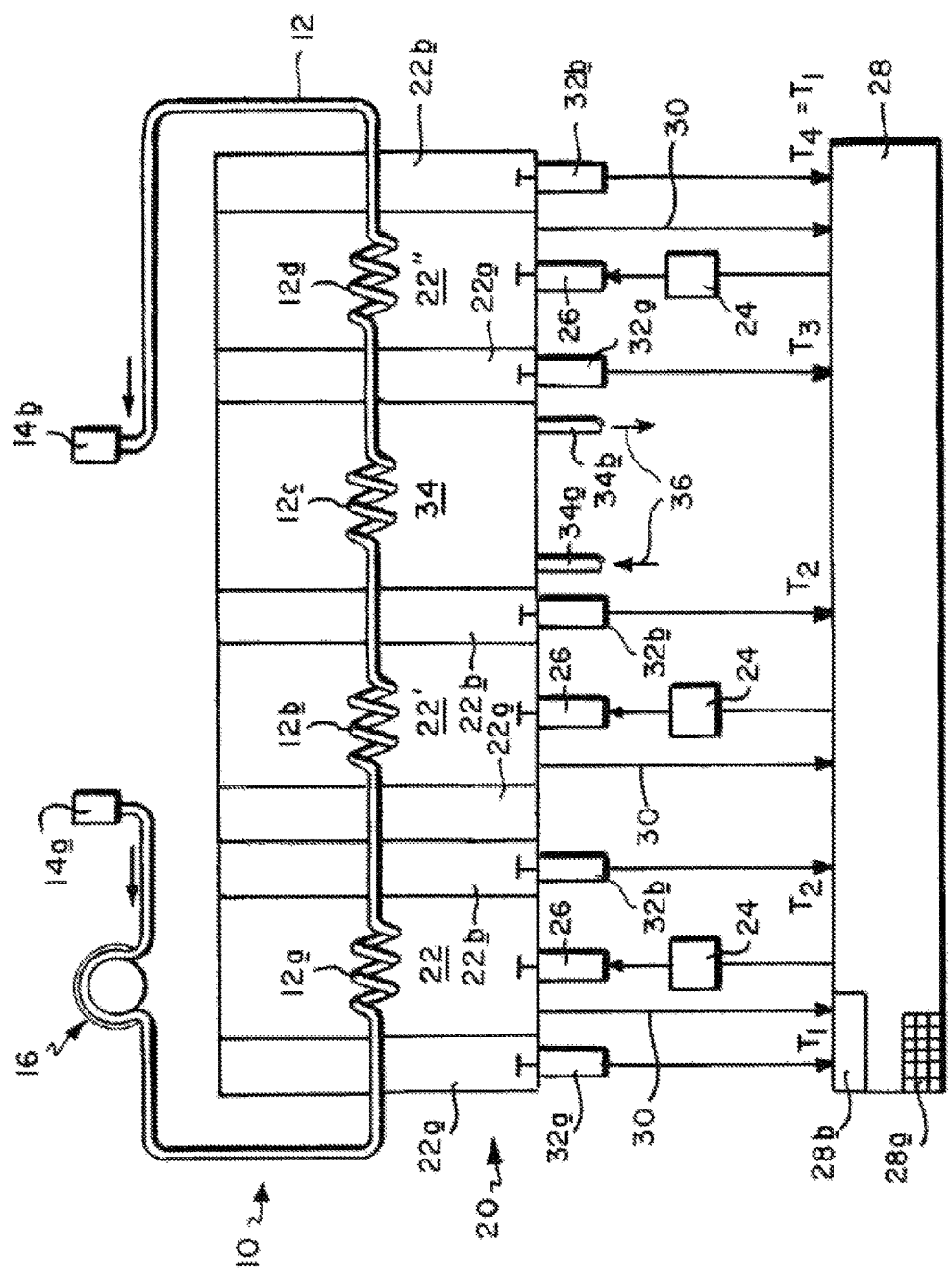
FIG. 1 is a schematic drawing of the device of the present invention.

Referring to FIG. 1, the blood is flowed through a cartridge unit shown generally at 10. The illustrated cartridge unit 10 includes dielectric tubing 12 with four tubing coils 12a, 12b, 12c, and 12d in series. The cartridge unit 10 may consist of four separate cartridges as depicted in FIG. 1 connected in series or it may be formed with a continuous length of tubing 12. In either event, the tubing 12 ends at the opposite ends of the series are provided with conventional connectors 14a and 14b to enable the cartridge unit 10 to be connected to a blood source and destination. In the preferred embodiment, connector 14a is connected to a patient through tubing to receive the patient's untreated blood in a manner as is known in the art, for example, as used in a hemodialysis device for extracting blood to be filtered, and connector 14b is coupled to a cannula inserted intravenously into the patient to receive the treated blood. Alternatively, connector 14a may be connected to a blood bag full of blood product and connector 14b may be coupled to an empty blood bag. If desired, a non-invasive flow regulator or peristalic pump 16 may be provided to control the flow of blood through tubing 12. Preferably, the blood should flow through the tubing 12 at a substantially constant velocity. Moreover, the cross section of the tubing 12 must remain substantially uniform and fixed throughout the system to prevent turbulence, which could otherwise create air emboli.

Cartridge unit 10 is arranged to be used in conjunction with the heating/cooling apparatus shown generally at 20. Apparatus 20 includes a first microwave heating chamber 22 having an inlet waveguide 22a and an outlet waveguide 22b and an aperture for receiving the cartridge unit coil 12a. Microwave energy from a microwave transmitter 24 is coupled to heating chamber 22 by way of a standard launch or probe 26 that projects into chamber 22. Transmitter 24 may be controlled by a controller 28 having a control panel or keyboard 28a.

The temperature of the blood flowing through the tubing coil 12a in the first microwave heating chamber 22 is monitored radiometrically using a sensing probe (not shown) similar to probe 26 which is connected by a coaxial conductor 30 to a radiometer 28b in controller 28. Similar sensing probes 32a and 32b are present in the inlet and outlet waveguides 22a and 22b to monitor the temperature of the blood in tubing 12 entering and leaving chamber 22. The controller 28 responds to the temperature measurements provided by the various sensing probes to control the power of the microwave energy injected into the first microwave heating chamber 22 via launch probe 26 so as to raise the temperature of the blood flowing through the tubing coil 12a from an initial value $T_1$ which is body temperature (about 37° C.), to a selected value $T_2$ sufficient to inactivate viruses in the blood product, e.g., 77° C. The construction and operation of the first microwave heating chamber 22, with its probes, radiometric circuitry and controller, is described in detail in the above U.S. Pat. No. 5,073,167, which is incorporated herein by reference.

Apparatus 20 further includes a dwell chamber 22' having an aperture for receiving the cartridge unit coil 12b. The dwell chamber 22' may be substantially identical to the first microwave heating chamber 22. Accordingly, its components have the same numeric identifiers as the corresponding components in chamber 22. Note that the dwell chamber 22' does not have a sensing probe 32a present in its inlet waveguide since the temperature of the blood in tubing 12 entering chamber 22' is identical to the temperature of the blood in tubing 12 exiting chamber 22. Alternatively, the dwell chamber 22' may be a preheated insulated chamber that uses means other than microwave heating to maintain its internal temperature at $T_2$. The function of the dwell chamber 22' is to controllably maintain the temperature of the column of blood flowing through tubing 12 after the blood has been heated in the first microwave heating chamber 22. When the blood leaves the dwell chamber 22' it has the same temperature $T_2$ as it had when entering the dwell chamber 22'. The flow rate of the blood and the length of tubing 12 within the dwell chamber 22' determines the duration of time that the blood is exposed to the desired virus destroying temperature $T_2$. This time may be a matter of only a fraction of a second to a few seconds.

Apparatus 20 also includes a cooling chamber 34 with an aperture for receiving the tubing coil 12c. Chamber 34 is provided with an inlet tube 34a and an outlet tube 34b by which a coolant 36 may be circulated through chamber 34 in order to rapidly, e.g., 1 second or less, cool the blood exiting dwell chamber 22' to a non-destructive temperature $T_3$ which may be somewhat below the ultimate delivery temperature, e.g., to 30° C.

The illustrated cartridge unit 10 has, in addition, a fourth tubing coil 12d which is adapted to be received in a fourth chamber 22" of apparatus 20. Chamber 22" is a second microwave heating chamber which may be substantially identical to the first microwave heating chamber 22. Accordingly, its components have the same numeric identifiers as the corresponding components in chamber 22. Its function is to controllably heat the column of blood flowing through tubing 12 after the blood has been cooled in cooling chamber 34. Using this 4-stage apparatus, the blood, having been overcooled in chamber 34, is heated in the second microwave heating chamber 22" so that when the blood leaves apparatus 20 it has a desired delivery temperature $T_4$ which should be the same as the initial temperature $T_1$, that is, body temperature (about 37° C.). Allowing overshoot during cooling provides more rapid cooling and, in turn, better control of the duration of the short-line heating to reach the desired delivery temperature.

During operation of apparatus 20, the blood is flowed through cartridge unit 10 at a predetermined velocity. That velocity and the tubing 12 dimensions determine the residence time of the blood in each of the four chambers. Thus, by presetting those parameters and controlling the power of the microwave energy in chambers 22 and 22', the time/temperature profile of the moving column of blood may be shaped to produce viral inactivation without undue cell damage.

The above described in-line cooling of the blood following heating allows the blood to be heated to temperatures previously assumed prohibited because, in the present apparatus 20, the heat exposure will be determined solely by the microwave power applied in chambers 22 and 22' to the blood and the flow rate, bearing in mind that only a small amount of blood is heated at any given moment in the cartridge coils 12a and 12b in chambers 22 and 22', respectively. Because such a small blood volume is involved, the warm-up time is very short and there is essentially no hold up time because the blood is always moving through the apparatus 20. Finally, due to the nature of the apparatus 20, the blood is subjected to uniform and closely controlled heating for the reasons stated above.

Figure 2:
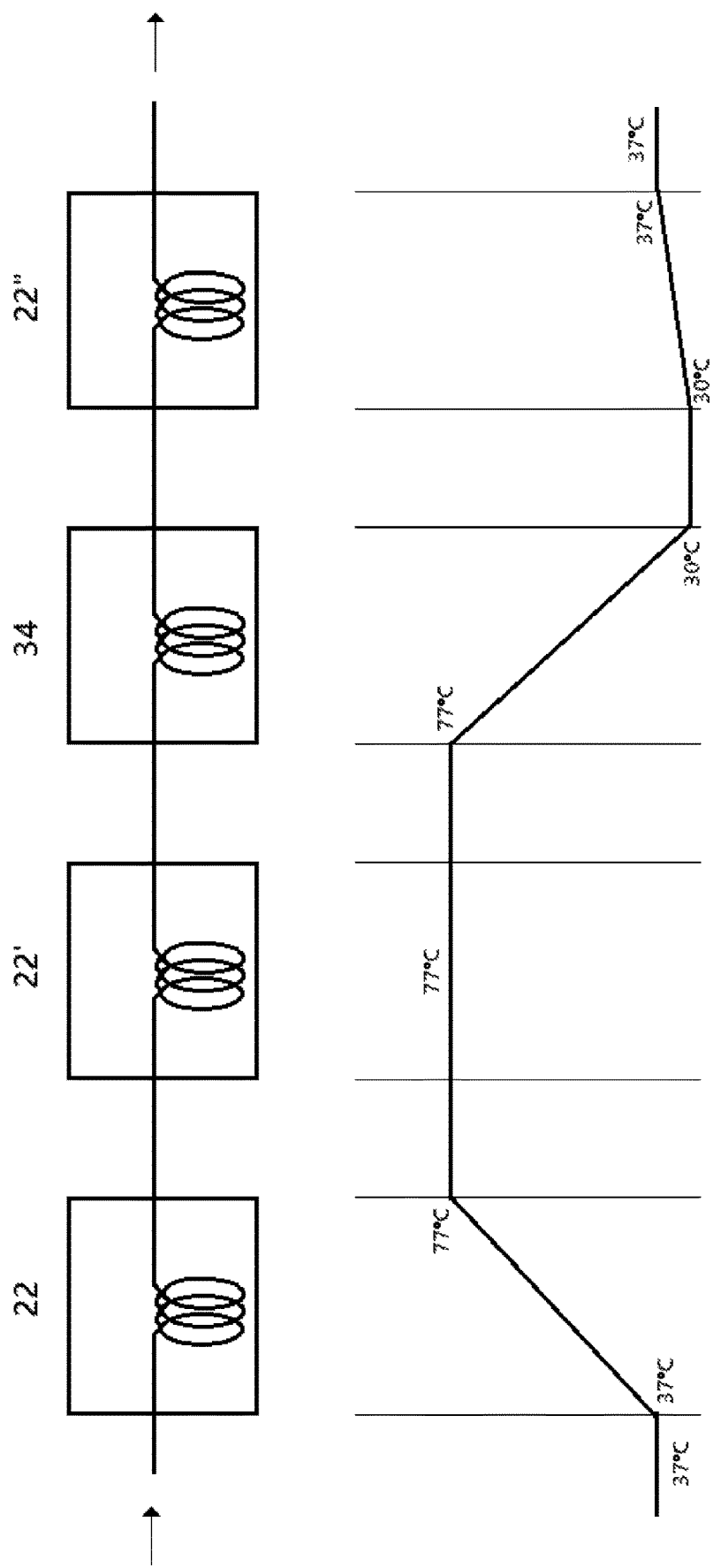
FIG. 2 is a schematic drawing of the temperature profile of the blood as it passes through the various chambers of the apparatus of the present invention.

FIG. 2 illustrates the temperature profile of the blood as is passes through the various chambers 22,22',34,22" of the apparatus 20. Initially, before the blood enters the first microwave heating chamber 22, it is at normal body temperature (about 37° C.), having just been extracted from the patient. Upon entering the first microwave heating chamber 22, the blood is rapidly heated to the desired temperature for destroying virus activity. As shown in Figure two, this may be 77° C., but other temperatures may also be sufficient for destroying virus activity without overheating the blood, for example, temperatures within the range of 75° C. to 85° C. Once the blood has been heated to the desired temperature by the first microwave heating chamber 22, it passes into the dwell chamber 22', where the desired temperature is maintained for a period of time. That period of time may be several seconds, enough for the heat to destroy the virus activity in the blood. Once the blood has been exposed to the desired temperature for the desired period of time, the blood passes into the cooling chamber 34, where the temperature of the blood is rapidly dropped to a temperature below the normal body temperature. As shown in Figure two, this may be 30° C., but other temperatures may also be sufficient, for example, temperatures within the range of 10° C. to 35° C. Finally, the blood passes into the second microwave heating chamber 22", where it is brought up to normal body temperature, thus making it safe to reintroduce into the patient. Where the apparatus 20 is used to destroy viruses in stored blood product, the initial temperature and the final temperature may be other than normal body temperature; for example, the initial temperature of the blood may be 10° C. or so if the blood source was from a blood bag, and the final temperature may be significantly cooler than that if the blood destination is another blood bag slated for refrigeration.

The present invention also contemplates a method of treating a patient infected by a blood-borne virus. The method involves the following steps:

Step A: Procure a device as described herein;

Step B: Connect the inlet end of the tubing of the device to a patient infected by a blood-borne virus, in a manner well known in the art, for example, as is used for hemodialysis treatment of kidney disease;

Step C: Initiate the flow of blood from the patient to the device;

Step D: Subject the blood to rapid heating, maintenance of the elevated temperature, cooling, and then reheating to return to normal body temperature, by the means of operating the device as described herein; and Step E: Return the blood through the outlet end of the tubing of the device to the patient by means of a cannula placed into the patient.

It will thus be seen that the objects set forth above, among those made apparent from the preceding description, are efficiently attained. Also, certain changes may be made in carrying out the above method and in the construction set forth without departing from the scope of the invention. Therefore, it is intended that all matter contained in the above description or shown in the accompanying drawing shall be interpreted as illustrative and not in a limiting sense. It is also to be understood that the following claims are intended to cover all of the generic and specific features of the invention described herein.

I claim:

1. A heat treatment apparatus for achieving viral inactivation in blood, said apparatus comprising
    a length of small diameter dielectric tubing having opposite ends and formed into a series of coils including a first coil, a second coil, and a third coil;
    a first connector mounted to a first end of the tubing for connecting the tubing to a blood source and a second connector mounted to a second end of the tubing for connecting the tubing to a blood destination;
    flow means for flowing blood product from said blood source within said tubing from the first end of the tubing to the second end of the tubing at a selected flow rate;
    a first electromagnetic heating chamber enclosing said tubing, said chamber having an access opening receiving said first coil into said first electromagnetic heating chamber;
    a first energy producing means connected to said first electromagnetic heating chamber for providing electromagnetic energy to said first electromagnetic heating chamber to heat the blood flowing in said first coil from an initial temperature to a selected elevated temperature sufficient for viral inactivation;
    a dwell chamber enclosing said tubing, said chamber having an access opening receiving said second coil into said dwell chamber;
    a second energy producing means connected to said dwell chamber for providing energy to said dwell chamber to maintain the blood flowing in said second coil at said selected elevated temperature sufficient for viral inactivation;
    a cooling chamber adjacent to said dwell chamber and enclosing said tubing, said cooling chamber having an access opening for receiving said third coil into said cooling chamber;
    cooling means connected to said cooling chamber for cooling the blood flowing in the third coil;
    means in said first electromagnetic heating chamber, said dwell chamber, and said cooling chamber for radiometrically monitoring the temperatures of the blood flowing in said first, second, and third coils, and producing first, second, and third temperature signals in response thereto; and
    control means connected to said monitoring means and responsive to the first, second, and third temperature signals for controlling the flow means, energy producing means and/or cooling means to impart a selected time-temperature profile to blood flowing within the tubing.

2. The heat treatment apparatus of claim 1 wherein
    the length of tubing further includes a fourth coil, said fourth coil located between the third coil of the tubing and the second end of the tubing;
    the heat treatment apparatus further comprises
        a second electromagnetic heating chamber adjacent to the cooling chamber and having an access opening for receiving said fourth coil into said second electromagnetic heating chamber,
        a third energy producing means connected to said second electromagnetic heating chamber for providing electromagnetic energy to said second electromagnetic heating chamber to heat the blood flowing in said fourth coil, and
    means in said second electromagnetic heating chamber for radiometrically monitoring the temperature of the blood flowing in said fourth coil, and producing a fourth temperature signal in response thereto; and
    the control means further delivers the blood to the fourth coil at a selected temperature below body temperature and controls the third energy producing means in response to the fourth temperature signal so as to reheat the blood flowing in the fourth coil to body temperature whereby the body temperature is approached from below.

3. The heat treatment apparatus of claim 2 wherein the second electromagnetic heating chamber further comprises an inlet waveguide; and the third energy producing means comprises a microwave transmitter coupled to the second electromagnetic heating chamber by way of a probe that projects into said chamber.

4. The heat treatment apparatus of claim 2 wherein the temperature of the blood achieved by the second energy producing means is substantially normal body temperature within the range of 36° C. to 38° C.

5. A method for treating a patient infected by a blood-borne virus, said method comprising the following steps:
   Step A: procure the heat treatment apparatus of claim 2;
   Step B: connect the first end of the tubing of the heat treatment apparatus to the patient;
   Step C: initiate the flow of blood from the patient to the heat treatment apparatus;
   Step D: subject the blood to heating within the first electromagnetic heating chamber of the heat treatment apparatus until a desired therapeutic temperature for the blood is achieved;
   Step E: maintain the blood at a constant temperature substantially equivalent to said desired therapeutic temperature within the dwell chamber of the heat treatment apparatus for a predetermined duration of time;
   Step F: subject the blood to cooling within the cooling chamber of the heat treatment apparatus until a desired cooling temperature for the blood is achieved, said cooling temperature being less than normal body temperature;
   Step G: subject the blood to heating within the second electromagnetic heating chamber of the heat treatment apparatus until the blood achieves normal body temperature; and
   Step H: return the blood through the second end of the tubing of the heat treatment apparatus to the patient by means of a cannula placed into the patient.

6. The method of claim 5 wherein the first electromagnetic heating chamber further comprises an inlet waveguide; and
   the first energy producing means comprises a microwave transmitter coupled to the dwell chamber by way of a probe that projects into said chamber;
   whereby the blood is heated in Step D by the first energy producing means.

7. The method of claim 5 wherein the second energy producing means provides electromagnetic energy to said dwell chamber;
   the dwell chamber further comprises an inlet waveguide; and
   the second energy producing means comprises a microwave transmitter coupled to the dwell chamber by way of a probe that projects into said chamber;
   whereby the blood is maintained at temperature in Step E by the second energy producing means.

8. The method of claim 5 wherein
   the dwell chamber is insulated and preheated to the selected elevated temperature sufficient for viral inactivation by the second energy producing means;
   whereby the blood is maintained at temperature in Step E by the second energy producing means.

9. The method of claim 8 wherein said second energy producing means comprises one or more radiant heating elements.

10. The method of claim 8 wherein said second energy producing means comprises a means for flowing a heated liquid or gas into and through the dwell chamber.

11. The method of claim 5 wherein the blood is cooled in Step F by circulating a coolant through the cooling chamber.

12. The method of claim 5 wherein the second electromagnetic heating chamber further comprises an inlet waveguide; and
   the third energy producing means comprises a microwave transmitter coupled to the dwell chamber by way of a probe that projects into said chamber;
   whereby the blood is heated in Step G by the third energy producing means.

13. The method of claim 5 wherein the temperature of the blood is radiometrically monitored in Steps D, E, and G.

14. The method of claim 5 wherein the temperature of the blood is radiometrically monitored in Step F.

15. The heat treatment apparatus of claim 1 wherein the flow means comprises a peristaltic pump.

16. The heat treatment apparatus of claim 1 wherein the selected elevated temperature of the blood achieved by the first energy producing means is within the range of 75° C. to 85° C.

17. The heat treatment apparatus of claim 1 wherein the selected elevated temperature of the blood maintained within the dwell chamber is within the range of 75° C. to 85° C.

18. The heat treatment apparatus of claim 1 wherein the temperature of the blood achieved by the cooling means is within the range of 10° C. to 35° C.

19. The heat treatment apparatus of claim 1 wherein the blood has a rate of flow within the tubing of between 200 ml/minute and 500 ml/minute.

20. The heat treatment apparatus of claim 1 wherein the tubing has a substantially uniform cross section.

21. The heat treatment apparatus of claim 1 wherein
   the blood source is a patient, wherein the first connector interacts with a blood extraction means, said blood extraction means suitably configured to extract blood from the patient in a substantially continuous manner; and
   the blood destination is the patient, wherein the second connector interacts with a blood reintroduction means, said blood reintroduction means suitably configured to reintroduce blood into the patient in a substantially continuous manner.

22. The heat treatment apparatus of claim 1 wherein the first electromagnetic heating chamber further comprises an inlet waveguide; and
   the first energy producing means comprises a microwave transmitter coupled to the first electromagnetic heating chamber by way of a probe that projects into said chamber.

23. The heat treatment apparatus of claim 1 wherein
   the second energy producing means provides electromagnetic energy to said dwell chamber;
   the dwell chamber further comprises an inlet waveguide; and
   the second energy producing means comprises a microwave transmitter coupled to the dwell chamber by way of a probe that projects into said chamber.

24. The heat treatment apparatus of claim 1 wherein
   the dwell chamber is insulated and preheated to the selected elevated temperature sufficient for viral inactivation by the second energy producing means.

25. The heat treatment apparatus of claim 24 wherein
   said second energy producing means comprises one or more radiant heating elements.

26. The heat treatment apparatus of claim 24 wherein
   said second energy producing means comprises a means for flowing a heated liquid or gas into and through the dwell chamber.

27. The heat treatment apparatus of claim 1 wherein
the cooling chamber comprises an inlet tube and an outlet tube; and
the cooling means comprises a coolant that is introduced into the cooling chamber through the inlet tube and circulated through the cooling chamber and then removed from the cooling chamber through the outlet tube.

\* \* \* \* \*

UNITED STATES PATENT AND TRADEMARK OFFICE
CERTIFICATE OF CORRECTION

| | |
|---|---|
| PATENT NO. | : 11,413,404 B2 |
| APPLICATION NO. | : 17/406556 |
| DATED | : August 16, 2022 |
| INVENTOR(S) | : Kenneth L. Carr |

It is certified that error appears in the above-identified patent and that said Letters Patent is hereby corrected as shown below:

On the Title Page

Item (12), delete "Carr Jr." and insert --Carr--

Item (72), reads:
Kenneth L. Carr Jr., Woolwich, ME (US)
Should be corrected to read:
Kenneth L. Carr, Woolwich, ME (US)

Signed and Sealed this
Twentieth Day of September, 2022

Katherine Kelly Vidal
*Director of the United States Patent and Trademark Office*